United States Patent

Killander et al.

[11] Patent Number: 5,707,399
[45] Date of Patent: Jan. 13, 1998

[54] ARRANGEMENT FOR FIXING ONE OR MORE ELECTRODE LEADS IN AN IMPLANTABLE MEDICAL DEVICE, SUCH AS A HEART STIMULATOR

[75] Inventors: Fredrik Killander, Taby; Karin Lungström, Hasselby; Per Jarl, Järfälla, all of Sweden

[73] Assignee: Pacesetter AB, Solna, Sweden

[21] Appl. No.: 634,619

[22] Filed: Apr. 18, 1996

[30] Foreign Application Priority Data

Apr. 18, 1995 [SE] Sweden .................. 9501405-6

[51] Int. Cl.$^6$ .................................. A61N 1/372
[52] U.S. Cl. ................................................ 607/37
[58] Field of Search ........................... 607/37, 36, 38, 607/9

[56] References Cited

U.S. PATENT DOCUMENTS 4,848,346  7/1989  Crawford .
4,860,750  8/1989  Frey et al. .
5,261,395  11/1993  Oleen et al. .
5,413,595  5/1995  Stutz, Jr. .......................... 607/37

FOREIGN PATENT DOCUMENTS 0 590 756    4/1994   European Pat. Off. .
WO 95/10324  4/1995   WIPO .

Primary Examiner—Scott M. Getzow
Attorney, Agent, or Firm—Hill, Steadman & Simpson

[57] ABSTRACT

An appliance for fastening one or more electrode leads in a connector unit of an implantable medical device, for example a heart stimulator, is formed of a wire- or strip-shaped resilient locking member, which is arranged to be inserted and fixed in a cavity in a connector unit, and which is shaped to clampingly engage diametrically opposed circumferential parts of the casing of each electrode lead.

33 Claims, 2 Drawing Sheets

ARRANGEMENT FOR FIXING ONE OR MORE ELECTRODE LEADS IN AN IMPLANTABLE MEDICAL DEVICE, SUCH AS A HEART STIMULATOR

BACKGROUND OF THE INVENTION

1. Field of the Invention

The present invention relates to an apparatus for fastening at least one electrode lead in an insertion hole in a connector unit of an implantable medical device, e.g. a heart stimulator, such as a pacemaker or defibrillator.

2. Description of the Prior Art

It is important during the connection of the proximal end of one or more electrode leads or conductors to the connector of a heart stimulator that each lead end is axially and radially securely held in the connector in order to ensure a good electrical contact and in order to prevent detaching of the electrode lead end from the connector.

In a known electrode lead fixing means, the electrode end is inserted into a hole in the connector which is adapted to the diameter of the end of the electrode, the end of the electrode being radially held fast in the hole. The axial locking or fastening of the end of the lead is achieved with the aid of a set screw, which is screwed into a transverse threaded hole in order to radially press a male plug part on the end of the electrode lead from one side against an opposing wall of a socket. This lamps the end of the lead and thus also serves to axial fasten the lead end in the hole. The use of a screw requires tools for the assembly and requires precise instructions and a precise tightening force on the screw.

U.S. Pat. No. 4,848,346 discloses a pacemaker connector system which eliminates problems associated with set screw systems. In this device the connector block firmly holds two circular springs which can be expanded to allow insertion of the heart lead by depressing a straight end portion of the spring which protrudes from the outer surface of the connector block. Such protruding end portions, however, may cause unintentional actuation of the springs and inadvertent release of the cardiac lead.

It has also been suggested to use a wedge element (U.S. Pat. No. 4,860,750) in order to fix the ends of the electrode conductors in the connector of the heart stimulator. Such a wedge element is insertable into a complementary channel which is orientated transversely and tangentially relative to the hole into which the electrode lead end is inserted, and has a cam profile with a concave seating surface in order to clamp the lead end through the lead casing when the wedge element is inserted. In this way the wedge element firmly holds the electrode lead in the hole from one side of the hole by means of elastic deformation of the lead end casing, which normally is made of a layer of silicon rubber. With this wedge-shaped embodiment of the locking or fixing element the fastening of the ends of the electrode leads is achieved by means of a single-sided, asymmetric type of fixing element which cannot guarantee a constant wedging force within the tolerance range for electrode leads.

European Application 0 590 756 describes a fixing arrangement for an electrode lead in a connector of a heart stimulator. The fixing arrangement is formed of a spring plate with opposing resilient gripping means cast in a connector, which is intended to cooperate with the contact pin on the lead and simultaneously prevent the end of the electrode lead from being pulled out of the connector. The retention force on the clamp increases when a withdrawing force is exerted on the electrode lead. The engagement of the gripping means on the contact pin of the lead end can be released when a force is exerted on opposing, projecting side tabs on the spring plate.

SUMMARY OF THE INVENTION

An object of the present invention is to provide an improved and simplified fixing means which can symmetrically clamp the end of the electrode lead on opposing sides with a constant force within the tolerance range for the lead, and which cannot be released if a clamping pressure is exerted upon the connector.

For this purpose the appliance of the present invention includes a resilient locking member insertable into a slot in the connector unit, the slot being formed to hold the locking member in a plane substantially normal to a longitudinal axis of the bore. The locking member is adapted, upon insertion thereof into the slot, to straddle and resiliently snap over an insulating cover of the electrode lead so as to firmly hold diametrically opposite portions thereof.

In a suitable embodiment of the fixing means according to the invention for fixing of two or more electrode leads arranged one above the other, the resilient locking member is shaped to be successively pushed over the casings of the leads along a path which connects the central axes of the leads with alternating inward and outward spring biasing of two opposing, preferably wave-shaped side branches of the resilient member. Such an embodiment provides a very simple mounting of the locking element as well as clamping the lead ends with a constant force from two opposing sides.

In another suitable embodiment of the fixing means according to the invention the resilient member is shaped so as to snap over the casing of the electrode lead in a direction which is essentially transverse to a line which connects the central axes of adjacent leads. In this way the electrode lead ends can be clamped by successively pushing locking sections of the resilient locking member over the lead ends from the side. Such an embodiment also makes it possible to fasten three or even more electrode ends in a connector where the insertion holes for the respective lead ends do not have to lie in a straight line.

In yet a further embodiment of the fixing means according to the invention for fixing two electrode leads, the resilient element is S-shaped with two arcuate portions which open in opposing directions and which are joined by a web part. The resilient member is rotatable around a transverse axis which is essentially parallel with the longitudinal axis of the electrode lead in the web part, in a cavity of the connector, from a passive position to a lead-clamping locking position, preferably inset in the connector. The resilient locking member is placed in this cavity before the ends of the electrode leads are pushed into their respective connection holes, following which the resilient member is rotated to the locking position simply by pressing each of the arcuate ends in opposing directions.

In a further embodiment for fixing of a single electrode lead the resilient locking member has an arcuate part, shaped in order to be able to clamp against diametrically opposing parts of an insulating casing on the electrode lead and rotatable in a cavity in the connector about an axis which is essentially parallel with the longitudinal axis of the electrode lead, from a passive position to a lead-clamping locking position, preferably inset in the connector.

3 electrode leads, the connecting ends of which being fixed by a fixing appliance according to the invention.

Figure 2:
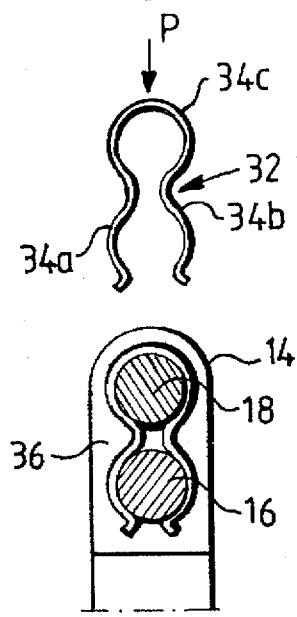

FIG. 2 is a schematic end view of the connector unit and a resilient locking member according to a first embodiment of the invention, before and after mounting.

Figure 3:
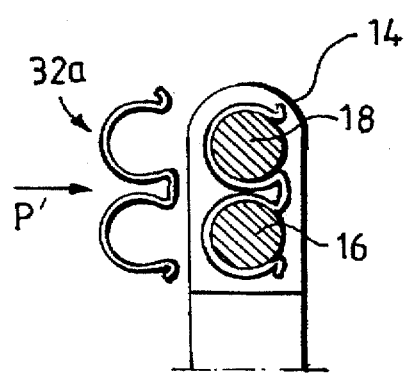

FIG. 3 is a view corresponding to FIG. 2 but showing a second embodiment of the resilient locking member according to the invention, before and after mounting.

Figure 4:
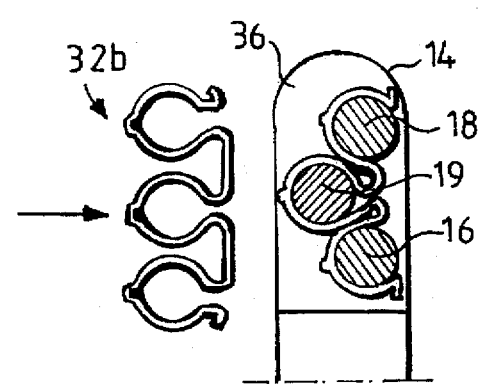

FIG. 4 is a view similar to FIGS. 2 and 3 but showing a third embodiment of the resilient locking member according to the invention, before and after mounting.

Figure 1:
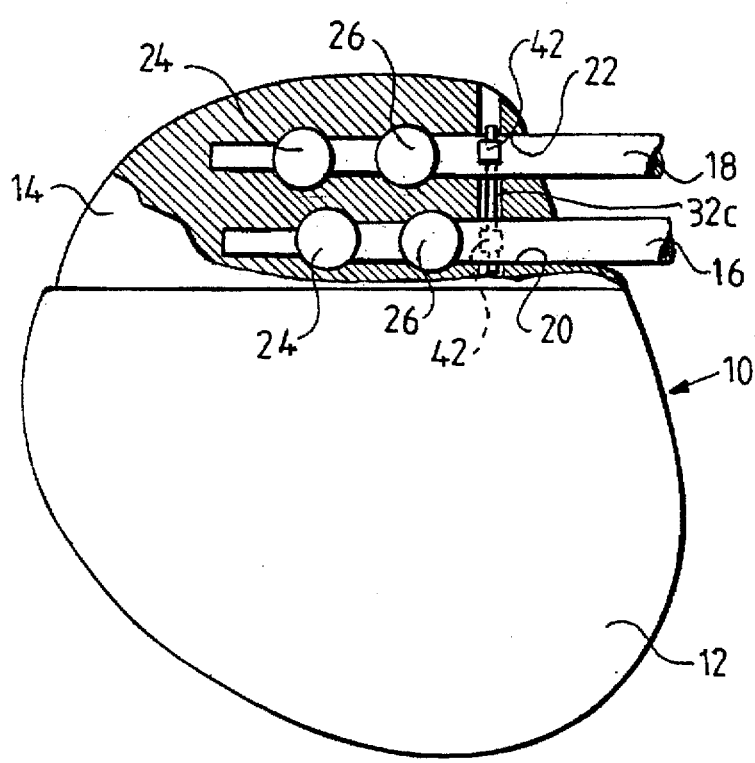
FIG. 1 schematically shows a side view of a pacemaker with an upper electrical connector unit for two bipolar
Figure 5:
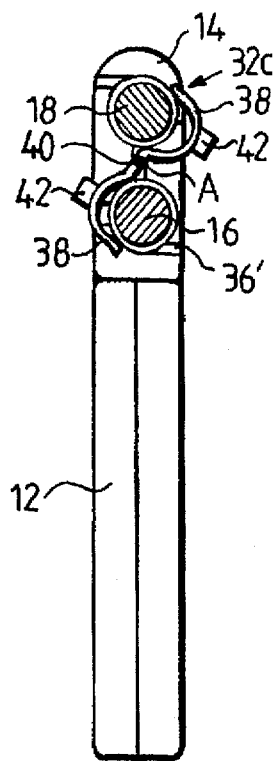

FIG. 5 is an end view of a pacemaker in FIG. 1 and shows a fourth embodiment of the resilient locking member according to the invention, in a position before fixing of the lead ends.

Figure 6:
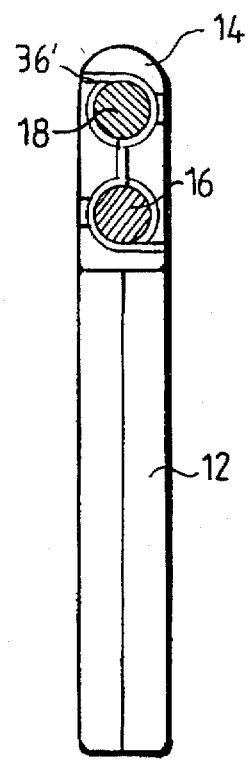

FIG. 6 is a view similar to FIG. 5 but showing the resilient locking member in the active locking position in the connector.

Figure 7:
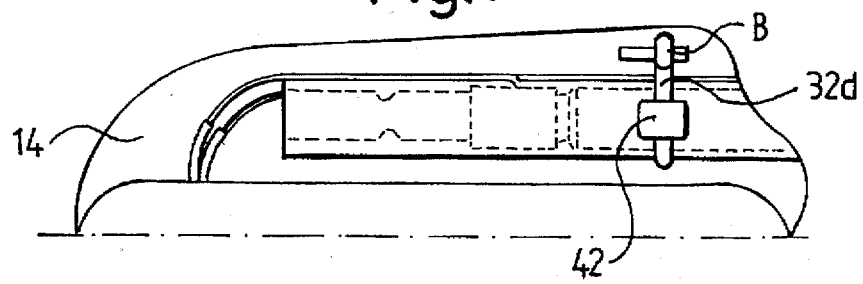

FIG. 7 shows a fifth embodiment of a resilient locking member according to the invention for mounting of a single electrode lead in a connector.

Figure 8:
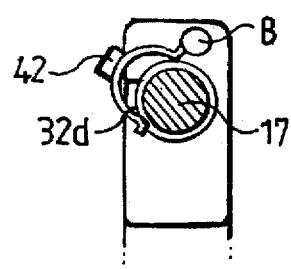

FIG. 8 is an end view of the resilient locking member in FIG. 7 in a position before fixing of the lead end.

Figure 9:
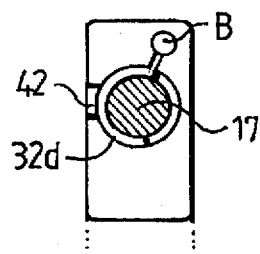

FIG. 9 is a view similar to FIG. 8 but showing the resilient locking member in the active locking position in the connector.

DESCRIPTION OF THE PREFERRED EMBODIMENTS

FIG. 1 shows an implantable pacemaker 10, having a casing 12, which encloses an electronic unit (not shown) with a pulse generator, and having a connector 14 in order to connect the electronic unit with, in this case, two proximal ends of bipolar electrical conductors 16 and 18, or so-called electrode leads. The leads are to be inserted through a peripheral vein and led via the upper carotid vein (vena cava superior) to the right side of the heart, where the electrodes at the distal lead end will come into contact with the heart muscle at a desired location.

There are two parallel blind holes 20 and 22 in the connector 14, which contain respective contact elements 24 and 26 for connection and contact with corresponding contact elements on the ends of the electrode leads 16 and 18, when these are inserted in the respective blind holes 20 and 22.

In order to attach the lead ends in the connector 14 according to the present invention to use a simple resilient locking member is used, which can partially surround diametrically opposing circumferential halves of the casing of the lead ends so as to clamp them with a constant force.

FIG. 2 shows a first embodiment of a simple resilient locking member 32 according to the invention for the simultaneous fastening of two electrode lead ends 16 and 18. The resilient member 32 is an elongated clip formed, for example, from a wire or a narrow strip of material suitable for the purpose, e.g. titanium, stainless spring steel or a plastic material, and has two essentially wave-shaped side branches 34a and 34b and a web part 34c joining them. The configuration of the side branches 34a and 34b and the web part 34c are therefore such that the casing of each of the lead ends 16 and 18 is subjected to symmetrical pressure forces directed toward each other, which are constant within the tolerance is range for the casing of the lead ends 16 and 18, when the resilient locking member 32 is mounted on them. In the embodiment in FIG. 2 the resilient locking member 32

4 is attached on the lead ends 16 and 18 is inserted in the connector 14 in the direction of arrow P in an exteriorly accessible slot 36 in the connector 14. The resilient member is pushed successively over the leads along a path which connects the central axes of the leads 16 and 18, with alternating springing in and out of the two opposing, wave-shaped side branches 34a and 34b on the resilient member 32. The slot 36 is shaped and dimensioned so that the resilient member 32 is held axially fixed therein. In this way, in the mounted condition, the lead ends 16 and 18 are radially held in the connector 14 through a tight fit in their respective holes 20 and 22, and axially fixed by means of the resilient member 32, of which the branches 32a and 32b are pressed somewhat into opposing side portions of the elastic outer casing, normally made of silicon rubber, of the electrode lead ends. In the active clamping position the resilient member 32 is enclosed within the outer contours of the connector 14, as shown in FIG. 2.

FIG. 3 shows a second embodiment of a resilient locking member 32a according to the invention for the simultaneous fastening of two electrode lead ends. Like the embodiment in FIG. 1 the resilient member 32a in this embodiment is formed of a wire- or strip-shaped resilient material, but it has a wavelike configuration. This configuration permits the resilient member to be pushed over the lead ends 16 and 18 in a lateral direction, essentially transverse to a line which connects the central axes of the leads, as is shown with arrow pr in FIG. 3. In this way the resilient member is first snapped over one lead end and subsequently over the other end while being inserted in the slot 36. In the mounted position the resilient member 32a is enclosed within the outer contour of the connector 14, as shown in FIG. 3, and presses into the opposing upper and lower portions of the elastic outer casing of the lead ends 16 and 18.

A third embodiment of a resilient member 32b according to the invention is shown in FIG. 4, where the ends of three electrode leads 16,18 and 19, which do not have to lie in the same vertical plane of the connector 14, are to be fastened in the connector 14. In principle, this embodiment is an extension of or an addition to the resilient member 32a in FIG. 3 with a further wave-shaped part. The snapping of the resilient member 32b over the lead ends occurs similarly in sequence in a slot 36 in the connector 14.

A fourth embodiment of a resilient member 32c according to the invention is shown in FIGS. 5 and 6, and consists of a wire or a strip element with two arcuate portions 38 facing in opposite directions and a straight web portion 40 connecting them. The resilient member 32c is inserted in a slot 36' in the connector 14 and is rotatable therein about an imaginary transverse axis A in the web portion 40 from a passive position shown in FIG. 5, in which the lead ends 16 and 18 can be inserted without any resistance into the contact position with the corresponding contact elements 24 and 26 in the connector 14 (FIG. 1), to a lead end clamping position retracted in the connector as is shown more clearly in FIG. 6. The arcuate parts 38 can be equipped with small pressing plates 42 in order to facilitate a manual locking of the resilient member 32c.

FIG. 7 shows a connector 14 for a single electrode lead 17 with a locking resilient locking member 32d according to a fifth embodiment of the invention. The locking member 32d has an arcuate part which in similarity with the embodiment in FIGS. 5 and 6 can be rotated about an axle or pin between a position shown in FIG. 8, in which the electrode lead end can be inserted into the insertion hole in the connector 14, and a fixing position according to FIG. 9 partially surrounding an electrode lead end casing. A pressure plate 42 similar to the embodiment according to FIGS. 5 and 6 can be arranged on the arcuate part in order to facilitate the manual locking of the resilient member 32d.

The embodiments of the resilient member according to the invention do not require any tools for mounting of the resilient member.

Although modifications and changes may be suggested by those skilled in the art, it is the intention of the inventors to embody within the patent warranted hereon all changes and modifications as reasonably and properly come within the scope of their contribution to the art.

We claim as our invention:

1. An arrangement for fixedly holding at least one electrode lead, having an insulating casing, comprising:

a connector unit of an implantable medical device with an insertion hole having a longitudinal axis;

said connector unit having a slot therein, accessible from an exterior of said connector unit, disposed in a plane substantially normal to said longitudinal axis of said insertion hole; and a resilient locking member insertable into said slot having two opposed side branches spaced from each other, said locking member, when inserted into said slot, comprising means for straddling and initially spreading apart over, and subsequently resiliently snapping over, said insulating casing of said electrode lead for non-invasively clamping directly against diametrically opposite portions of an exterior of said insulating casing of said electrode lead for holding said electrode lead in said connector unit.

2. An arrangement as claimed in claim 1 wherein said connector unit comprises two insertion holes for respectively receiving two electrode leads each having an insulating casing and each having a central axis, wherein said plane of said slot intersects both of said central axes of said electrode leads, and wherein said resilient member comprises means for successively sliding in said slot along a path intersecting said central axes with said opposing side branches alternatingly being biased inwardly and outwardly relative to said electrode leads to assume a position in said slot simultaneously firmly holding diametrically opposite portions of each of said electrode leads.

3. An arrangement as claimed in claim 2 wherein said side branches are wave-shaped.

4. An arrangement as claimed in claim 1 wherein said connector unit comprises two insertion holes for respectively receiving two electrode leads, each having an insulating casing and each having a central axis, said central axes intersecting said plane with said central axes being aligned in an alignment direction, and wherein said resilient member comprises means having a shape for simultaneously snapping over both of said electrode leads when pushed over the respective insulating casings of said electrode leads in a direction substantially transversely to said alignment direction for simultaneously firmly holding diametrically opposite portions of each of said electrode leads.

5. An arrangement as claimed in claim 4 wherein said resilient member comprises a resilient member having a wave-like configuration including adjacent sections with partially circular shapes for respectively partially surrounding a circumference of each electrode lead.

6. An arrangement as claimed in claim 1 wherein said connector unit comprises three insertion holes for respectively receiving three electrode leads, each electrode lead having a central axis and an insulating casing, and wherein said resilient member comprises means for snapping over each of said three electrode leads as said resilient member is pushed over the respective insulating casings in a direction substantially transverse to each longitudinal direction of each insertion hole for simultaneously firmly holding diametrically opposite portions of each of said three electrode leads.

7. An arrangement as claimed in claim 6 wherein none of the central axes of said electrode leads are aligned.

8. An arrangement as claimed in claim 6 wherein no more than two of said central axes of said electrode leads are aligned.

9. An arrangement as claimed in claim 1 wherein said resilient member comprises a resilient member which, when inserted in said slot, is completely enclosed within said connector unit.

10. An arrangement as claimed in claim 1 wherein said resilient member comprises a titanium resilient member.

11. An arrangement as claimed in claim 1 wherein said resilient member comprises a stainless steel resilient member.

12. An arrangement as claimed in claim 1 wherein said resilient member comprises a plastic resilient member.

13. An arrangement as claimed in claim 1 wherein said resilient member and said slot have respective dimensions so that said resilient member is tightly frictionally held in said slot.

14. An arrangement as claimed in claim 1 wherein said locking member comprises a wire.

15. An arrangement as claimed in claim 1 wherein said locking member comprises a thin strip.

16. An arrangement for fixing two electrode leads in a connector unit of an implantable medical device, said connector unit having two insertion holes, each having a longitudinal axis, for respectively receiving said two electrode leads, said arrangement comprising:

said connector unit having a recess therein;

an S-shaped elongated resilient locking member having two arcuate portions facing in opposite directions joined by a central web portion; and means for rotatably mounting said locking member at said web portion in said recess in said connector unit for permitting rotation of said locking member around a transverse axis extending substantially parallel to the longitudinal axes of the respective insertion holes from a passive position wherein said arcuate portions are free of electrode leads in said insertion holes to a clamping position wherein said arcuate portions respectively partially surround said electrode leads.

17. An arrangement as claimed in claim 16 wherein said locking member, when in said clamping position, is completely enclosed within said connector unit.

18. An arrangement as claimed in claim 16 wherein said locking member comprises a wire.

19. An arrangement as claimed in claim 16 wherein said locking member comprises a thin strip.

20. An arrangement as claimed in claim 16 wherein said resilient member comprises a titanium resilient member.

21. An arrangement as claimed in claim 16 wherein said resilient member comprises a stainless steel resilient member.

22. An arrangement as claimed in claim 16 wherein said resilient member comprises a plastic resilient member.

23. An arrangement as claimed in claim 16 wherein said locking member and said recess have relative dimensions so that said locking member is tightly frictionally held in said recess.

24. An arrangement as claimed in claim 16 wherein said recess comprises a slot.

25. An arrangement for fixing an electrode lead in a connector unit of an implantable medical device, said connector unit having an insertion hole, having a longitudinal axis, for receiving said electrode lead, said arrangement comprising:

a cavity in said connector unit;

an elongated resilient locking member having an arcuate portion shaped for clampingly engaging diametrically opposite portions of said electrode lead; and means for mounting said locking member for rotation in said cavity of said connector unit around an axis extending substantially parallel to said longitudinal axis of said insertion hole for permitting said locking member to move from a passive position, wherein said locking member is free of said electrode lead, to a locking position wherein said arcuate portion clampingly engages diametrically opposite portions of said electrode lead.

26. An arrangement as claimed in claim 25 wherein said locking member, when in said clamping position, is completely enclosed within said connector unit.

27. An arrangement as claimed in claim 25 wherein said locking member comprises a wire.

28. An arrangement as claimed in claim 25 wherein said locking member comprises a thin strip.

29. An arrangement as claimed in claim 25 wherein said resilient member comprises a titanium resilient member.

30. An arrangement as claimed in claim 25 wherein said resilient member comprises a stainless steel resilient member.

31. An arrangement as claimed in claim 25 wherein said resilient member comprises a plastic resilient member.

32. An arrangement as claimed in claim 25 wherein said locking member and said cavity have relative dimensions so that said locking member is tightly frictionally held in said cavity.

33. An arrangement as claimed in claim 25 wherein said cavity comprises a slot.

* * * * *